(12) United States Patent
Marino et al.

(10) Patent No.: US 7,658,748 B2
(45) Date of Patent: Feb. 9, 2010

(54) RIGHT RETRIEVAL MECHANISM

(75) Inventors: Joseph A. Marino, Apple Valley, MN (US); Michael P. Corcoran, Woodbury, MN (US)

(73) Assignee: Cardia, Inc., Burnsville, MN (US)

( * ) Notice: Subject to any disclaimer, the term of this patent is extended or adjusted under 35 U.S.C. 154(b) by 0 days.

(21) Appl. No.: 10/668,445

(22) Filed: Sep. 23, 2003

(65) Prior Publication Data

US 2005/0065548 A1 Mar. 24, 2005

(51) Int. Cl.
*A61B 17/08* (2006.01)
(52) U.S. Cl. ........................ 606/213; 606/215
(58) Field of Classification Search ................ 606/200, 606/213, 215, 153, 151
See application file for complete search history.

(56) References Cited

U.S. PATENT DOCUMENTS

| | | | |
|---|---|---|---|
| 3,874,388 A * | 4/1975 | King et al. .................. 606/232 |
| 4,007,743 A | 2/1977 | Blake | |
| 4,917,089 A | 4/1990 | Sideris | |
| 5,108,420 A * | 4/1992 | Marks ........................ 606/213 |
| 5,171,259 A | 12/1992 | Inoue | |
| 5,284,488 A | 2/1994 | Sideris | |
| 5,334,137 A | 8/1994 | Freeman | |
| 5,334,217 A | 8/1994 | Das | |
| 5,382,260 A | 1/1995 | Dormandy, Jr. et al. | |
| 5,397,331 A | 3/1995 | Himpens et al. | |
| 5,425,744 A | 6/1995 | Fagain et al. | |
| 5,433,727 A | 7/1995 | Sideris | |
| 5,451,235 A | 9/1995 | Lock et al. | |
| 5,634,936 A | 6/1997 | Linden et al. | |
| 5,649,950 A | 7/1997 | Bourne et al. | |
| 5,702,421 A * | 12/1997 | Schneidt ..................... 606/213 |
| 5,709,707 A * | 1/1998 | Lock et al. .................. 606/213 |
| 5,725,552 A | 3/1998 | Kotula et al. | |
| 5,733,294 A * | 3/1998 | Forber et al. ................ 606/151 |
| 5,741,297 A | 4/1998 | Simon | |
| 5,853,422 A * | 12/1998 | Huebsch et al. ............. 606/213 |
| 5,904,703 A | 5/1999 | Gilson | |
| 6,024,756 A | 2/2000 | Huebsch et al. | |
| 6,174,322 B1 | 1/2001 | Schneidt | |
| 6,206,907 B1 * | 3/2001 | Marino et al. ............... 606/215 |
| 6,261,309 B1 * | 7/2001 | Urbanski .................... 606/213 |
| 6,379,368 B1 | 4/2002 | Corcoran et al. | |
| 2001/0044634 A1 * | 11/2001 | Don Michael et al. ....... 606/200 |

FOREIGN PATENT DOCUMENTS

| | | |
|---|---|---|
| DE | 233 303 A1 | 2/1986 |
| DE | 4222291 | 1/1994 |
| EP | 0 362 113 A1 | 4/1990 |
| EP | 0 541 063 A2 | 12/1993 |
| EP | 0 541 063 A3 | 12/1993 |
| EP | 0 541 063 B1 | 2/1998 |
| GB | 2 269 321 A | 9/1994 |

* cited by examiner

*Primary Examiner*—Corrine M McDermott
*Assistant Examiner*—Christopher D Prone
(74) *Attorney, Agent, or Firm*—Kinney & Lange, P.A.

(57) ABSTRACT

An occlusion device for the closure of physical apertures, such as vascular or septal apertures, that can be retrieved, reloaded, and redeployed in situ. A plurality of puller arms and a floating center post allow the device to collapse for loading when a physician pulls on a delivery device, which is attached to the floating center post. This also allows for easy loading of the device into a catheter for delivery to the heart.

38 Claims, 6 Drawing Sheets

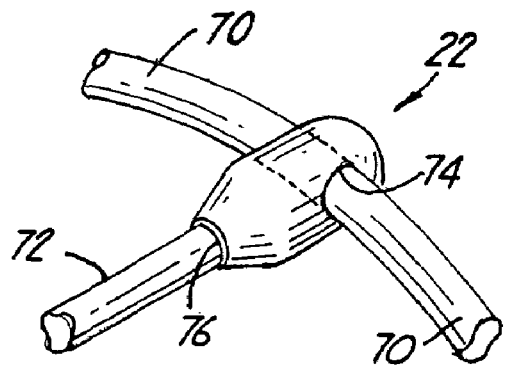
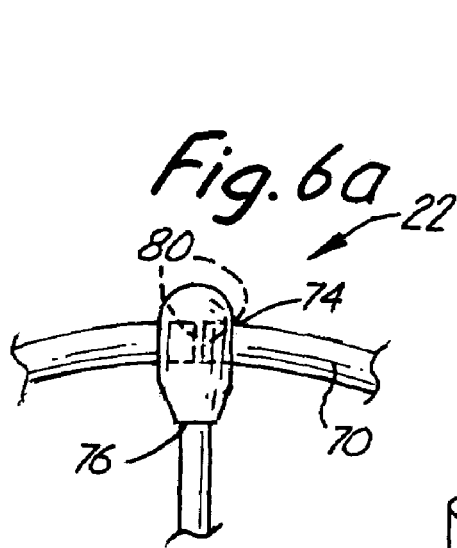
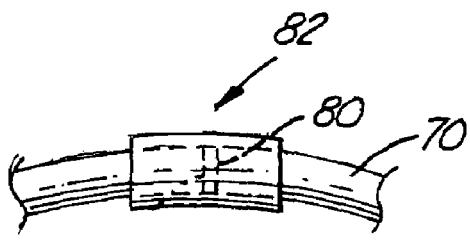
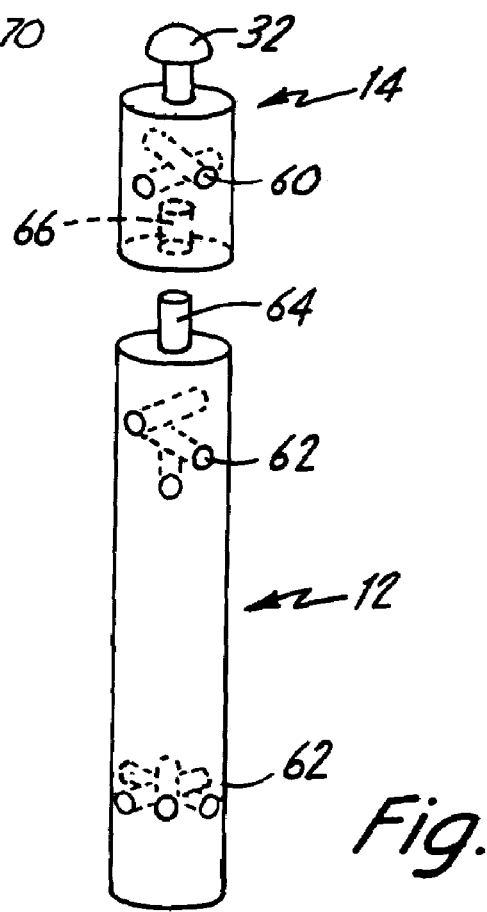
Fig. 5
Fig. 6a
Fig. 6b
Fig. 4

RIGHT RETRIEVAL MECHANISM

CROSS-REFERENCE TO RELATED APPLICATION(S)

None.

BACKGROUND OF THE INVENTION

This invention relates to an occlusion device for the closure of physical apertures, such as vascular or septal apertures. More specifically, this invention relates to an occlusion device for the heart that can be retrieved, reloaded, and redeployed in situ.

The heart is generally comprised of four chambers: the left and right atrium and the left and right ventricle. Separating the left and right sides of the heart are two walls, or septa. The wall between the two atria is the interatrial septum, and the wall between the two ventricles is the interventricular septum. There are several defects which can affect the septa of both children and adults, including patent ductus arteriosus, patent foramen ovale, atrial septal defects (ASDs), and ventricular septal defects (VSDs). Although the causes and physical characteristics of these defects vary by type, each of these defects is generally an aperture, flap, or hole in the septum which allows blood to shunt between chambers in the heart where there is no blood flow in a normal, healthy heart. This abnormal shunt can cause a variety of health problems.

Normally, permanently repairing certain cardiac defects in adults and children requires open heart surgery, which is a risky, painful, and expensive procedure. Surgery for closure of a heart defect is major heart surgery, which requires the patient to undergo general anesthesia and opening of the chest cavity. The patient must spend several days in the hospital and takes several weeks to be able to return to normal levels of activity.

To avoid the risks and discomfort associated with open heart surgery, modern occlusion devices have been developed that are small, implantable, and capable of being delivered to the heart through a catheter. Rather than surgery, a catheter inserted into a major blood vessel allows an occlusion device to be deployed by moving the device through the catheter to the treatment site within the body. This procedure is performed in a cardiac cathlab and avoids the risks, pain, and long recovery associated with open heart surgery.

There are currently several types of occlusion devices capable of being inserted via a catheter including button devices, collapsible umbrella-like structures, and plug-like devices. These modern occlusion devices can repair a wide range of cardiac defects, including patent foramen ovale, patent ductus arteriosus, atrial septal defects, ventricular septal defects, and may occlude other cardiac and non-cardiac apertures. One form of occlusion device generally has a left side, a right side, and a center section. Once the occluder is deployed, the left side sits in the left side of the patient's heart and the right side sits in the right side of the patient's heart. The occluder's center section extends through the center of the defect. The left and right sides occlude the aperture on the respective sides of the patient's septum.

To deploy the occlusion device, a physician loads the device into a catheter, advances the device via catheter to the treatment site, and deploys the device at the treatment site. Loading the device into the catheter must be done by hand, and requires a high degree of manual dexterity and takes time. Once the device is loaded, it is maneuvered through the catheter to the treatment site within the body. In the event the device is not deployed properly or effectively, it must be retrieved and the procedure must be performed again. Some of these devices are retrievable via catheter, but many require open heart surgery to be retrieved. Once retrieved, many types of occlusion devices cannot be redeployed. In such instances, a new occlusion device must be used, increasing the cost of the procedure.

Even if the device can be retrieved using a catheter, retrieval may require insertion of a larger diameter catheter. A larger diameter catheter may be needed because the device may not readily resume the compact shape it had before deployment. Once retrieved, the device may be compromised from the stress of withdrawing it back into the catheter, even if a larger diameter catheter has been used. As such, it may not be possible to reuse the retrieved occlusion device.

In addition, devices retrieved via catheter do not necessarily reload for redeployment when they are retrieved. Even if the device can be re-used, it must be completely removed from the catheter to be properly reloaded. Thus, even if the device is retrievable, the device must be pulled back through the catheter, removed, and reloaded. Once again, just as with the loading procedure, reloading is time consuming and requires high manual dexterity. This adds extra time to the procedure, and creates wear and tear on the device. Often, the retrieved device cannot be reused because it has been damaged by the retrieval process. If the device cannot be reused, a new device must be used, adding to the cost of the procedure.

Thus, there is a need in the art for an occlusion device that is easier to load into a catheter and can be retrieved, reloaded, and redeployed in situ.

BRIEF SUMMARY OF THE INVENTION

This invention relates to an occlusion device for the closure of physical apertures, such as vascular or septal defects. More specifically, this invention relates to a loading system for an occlusion device that allows the device be retrieved, reloaded, and redeployed in situ. The loading system comprises a plurality of puller arms and a floating center post to allow the device to automatically collapse for loading. The floating center post may be designed to work with a fixed center post present in the occlusion device. The design allows for easy loading as well as remote reloading and redeployment.

When the present invention is retrieved, it reloads and is ready for immediate redeployment. The device does not need to be pulled back through the catheter so that the physician can reload it for deployment. In addition, the present design makes initial loading of the device easier. Because the device can be remotely retrieved and reloaded, and then redeployed, it reduces procedure time, cost, and risk to the patient.

BRIEF DESCRIPTION OF THE DRAWINGS

FIG. 4 is a perspective view of a floating center post and a fixed center post.

FIG. 5 is a perspective view of an end cap in place on a hoop.

FIG. 6a is a top view of an end cap which demonstrates one method of closing a hoop.

FIG. 6b is a top view of a coupler which demonstrates one method of closing a hoop.

DETAILED DESCRIPTION

Figure 1:
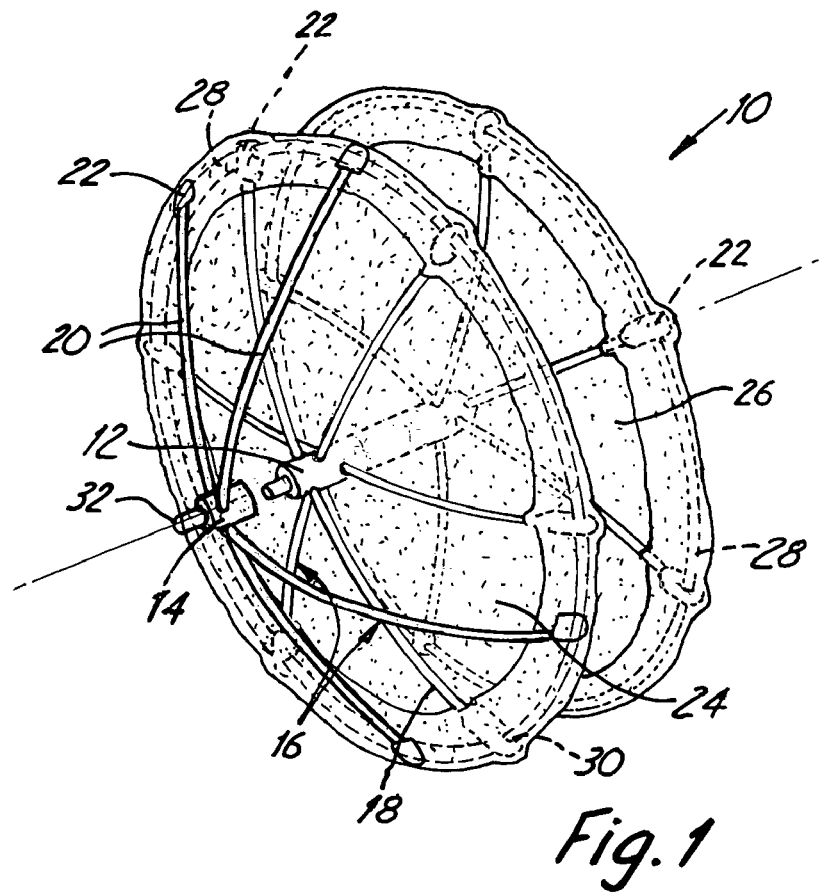
FIG. 1 is a perspective view of the top of an occlusion device.

FIG. 1 is a top perspective view of an occlusion device 10. The occlusion device 10 comprises a fixed center post 12, a floating center post 14, a right fixation device 16, wire arms 18, puller arms 20, and end caps 22. The right fixation device 16 is connected to the center post 12 and comprises six wire arms 18 which are capped with the end caps 22. The puller arms 20 are threaded through holes in the floating center post 14. The ends of the puller arms 20 are also capped with end caps 22. The occlusion device 10 also includes a right sheet 24, a left sheet 26, and wire hoops 28. The hoops 28 surround the perimeter of the right and left sheets 24, 26 and pass through holes 30 in the end caps 22. A grasping knob 32 is located at the tip of the floating center post 14.

Figure 2:
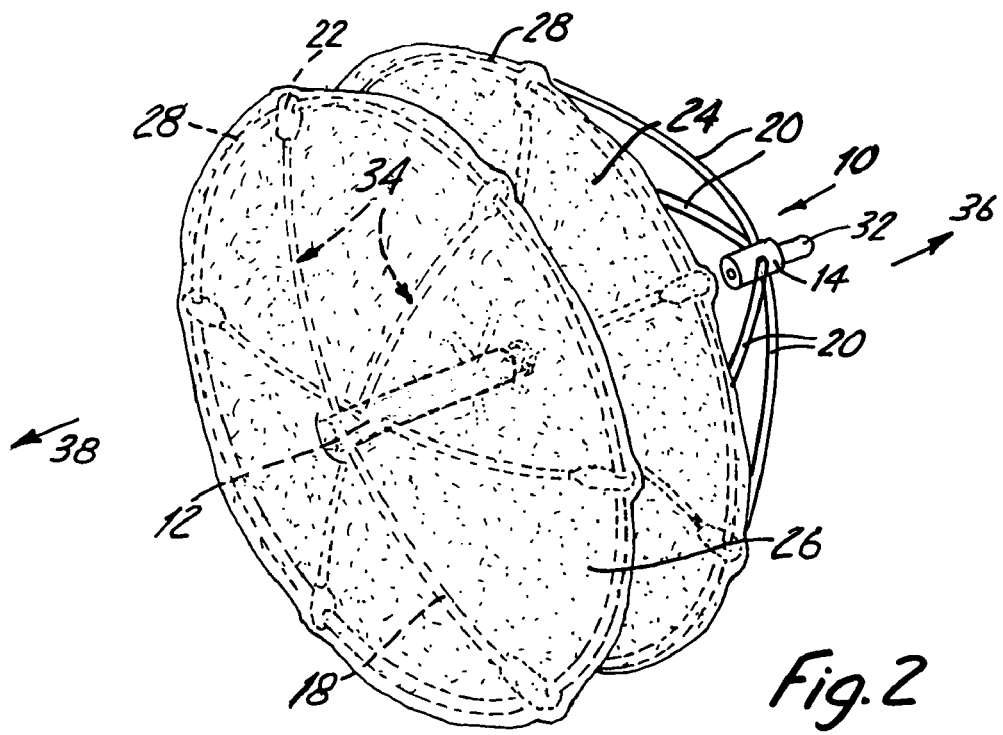
FIG. 2 is a perspective view of the bottom of an occlusion device.

FIG. 2 is a bottom perspective view of the occlusion device 10. FIG. 2 illustrates the center post 12, the left sheet 26, and a left fixation device 34. The left fixation device 34 also comprises six arms 18 which are capped by end caps 22. Also visible in FIG. 2 is the right sheet 24, the hoops 28, the floating center post 14, the grasping knob 32, and the puller arms 20.

Unlike the right fixation device 16 which is located on an outer side of the right sheet 24, the left fixation device 34 is located on an inner side of the left sheet 26. However, the device 10 is not so limited, and the fixation devices 16, 34 may be located on the outer side of the sheets 24, 26, on the inner side of the sheets 24, 26, or any combination thereof.

The right and left fixation devices 16, 34 are connected to the fixed center post 12. One method of connecting the right and left fixation devices 16, 34 to the fixed post 12 is to provide the fixed center post 12 with drill holes through which the fixation devices 16, 34 pass. When connected to the fixed center post 12 using holes drilled through the fixed center post 12, the fixation devices 16, 34 may be formed of three wires. The three wires create the six arms 18 because the post 12 divides each wire into two arms 18 when the wire passes through the center post 12.

The end caps 22 provide a location for connecting the ends of the arms 18 to the hoops 28. In addition, the end caps 22 located at the distal ends of the arms 16 serve to minimize damage to surrounding tissue once the device 10 is inserted.

The sheets 24, 26 are connected to the device 10 at the fixation devices 16, 34 and at the hoops 28. The sheets 24, 26 may be connected to the fixation devices 16, 34 using any suitable method. One method of attaching the sheets 24, 26 to the fixation devices 16, 34 is to suture the sheets 24, 26 to the arms 16 of the fixation devices 16, 34. The sheets 24, 26 may attach to the hoops 28 by folding each sheet 24, 26 over the perimeter of the hoop 28 and then securing the sheets 24, 26 in place. A variety of securing methods may be used such as suturing, heat treating, or laminating. Methods of attaching the sheets 24, 26 to the hoops 28 are described more fully in FIGS. 7 and 8.

The hoops 28 attach to the device at the end caps 22. The end caps 22 are provided with drilled holes 30 through which the hoops 28 can pass for attachment. The hoops 28 are constructed of a single, heat shaped wire which is threaded through the end caps 22 and then secured. Methods of securing the ends of the hoops 28 are described more fully in FIGS. 6a and 6b.

The knob 32 on the floating center post 14 is configured to allow the device 10 to be grasped by a forceps as it is guided through the catheter. However, the method of attachment to a delivery device is not so limited. The knob 32 may be modified as needed to attach to any delivery device. For instance, the knob 32 may be fitted with threads so that it may be screwed onto a delivery device that is outfitted with threads. Only one side of the device 10 requires a knob 32 or other mechanism to attach to a delivery device.

The device 10 is configured to be deployed through a catheter, and more specifically, the device 10 is constructed so that the fixation devices 16, 34 are easily collapsible about the fixed center post 12 to allow the device 10 to be inserted through a catheter. Due to this construction, the device 10 can be folded such that the right fixation device 16 is folded backwards in the axial direction 36, and the left fixation device 34 is folded in an opposite axial direction 38, which allows the folded device 10 to fit into a small diameter catheter. The right and left sheets 24, 26, attached to the fixation devices 16, 34, collapse as the fixation devices 16, 34 are folded. Likewise, the hoops 28 are also flexible and are configured to collapse.

Once the device 10 is deployed across a defect in the heart, the fixation devices 16, 34, the hoops 28, and the sheets 24, 26 unfold to form a seal around each side of the defect. To ensure the device 10 returns to a shape capable of exerting enough pressure to seal the defect, the fixation devices 16, 36 are made of a suitable material capable of shape memory, such as nickel-titanium alloy, commonly called Nitinol. Nitinol is preferably used because it is commercially available, very elastic, non-corrosive and has a fatigue life greater than that of stainless steel. To further ensure that the fixation devices 16, 34 do not suffer from fatigue failures, one embodiment of the present invention comprises making the wire fixation devices 16, 34 of stranded wire or cables.

The wire arms 18 are preferably subjected to precise pre-shaping to give them a "shape memory." The pre-shaping can be done using any suitable method, such as machining, heat treating, or both. The shape memory helps to hold the strands together when the arms 18 are formed of stranded wire or cable, and can be used to add pretension to the arms 18 so that they "remember" their shape even after undergoing a strong deformation when the device 10 is passed through a catheter. The end caps 22 may further serve to prevent potential unraveling of the arms 18 when the arms 18 are formed of stranded wire or cable.

The support hoops 28 are also made of a suitable material capable of shape memory, such as nickel-titanium alloy, like Nitinol. The hoops 28 may be constructed of a single wire or stranded wire. The diameter of the wire that is used to form the support hoops 28 must be small enough so that the hoops 28 are flexible enough to collapse when the device 10 is being loaded or retrieved. However, the wire must be stiff enough to allow the hoops 28 to lie as flat possible against the patient's septum to create an effective seal. Similar to the wire arms 18, the support hoops 28 may also be heat shaped or machine shaped so that the hoops 28 have shape memory to ensure that the hoops 28 resume the proper shape once the hoops 28 leave the catheter.

Another advantage of pre-shaping the hoops 28 using heat is to ensure that the hoops 28 are properly sized. If the hoops 28 are too large or too small for the device 10, the hoops 28 may pucker or may cause the sheets 24, 26 to pucker. If the hoops 28 or sheets 24, 26 pucker they cannot lie flat against the septum and therefore do not seal as effectively as the sheets 24, 26 can if the sheets 24, 26 lie flat and hug the septum.

The support hoops 28 allow the device 10 to hug the tissue surrounding the defect, creating a uniform seal around the opening of the defect, which improves the sealing capabilities of the occlusion device 10. The hoops 28 further serve to reduce the potential for increased pressure on surrounding tissue caused by one or more of the arms 18. More specifically, once deployed, the arms 18 of the fixation devices 16, 34 exert pressure on the hoops 28 and sheets 24, 26 to form a seal around the defect. Without the hoops 28, the highest points of pressure are the six or eight pressure points where the tips 22 of the arms 18 may press against the tissue surrounding the defect. Given the uneven topography of the heart, some arms 18 may put more pressure on surrounding tissue than others. Thus, instead of having six or eight pressure points, the support hoops 28 help distribute pressure more evenly around a continuous circle, decreasing the possibility that increased pressure will be exerted at any one contact point. By distributing pressure more evenly, the risk that one or more of the arms 18 will poke through tissue or poke through the defect is greatly reduced.

The sheets 24, 26 are preferably formed of a medical grade polymer. One suitable material is DACRON®. Preferably, the sheets 24, 26 are formed of a high density polyvinyl alcohol (PVA) foam, such as that offered under the trademark IVALON®. To minimize the chance of the device 10 causing a blood clot, the sheets 24, 26 may be treated with a thrombosis-inhibiting material. One such suitable material is heparin.

The size of the sheets 24, 26 may vary to accommodate various sizes of defects. In some instances, it may be desirable to form the sheets 24, 26 so that they are not both the same size. For instance, one sheet and its associated fixation device can be made smaller than the corresponding sheet and its associated fixation device. This is particularly useful in situations where the occlusion device 10 is to be placed at a location in the heart which is close to other nearby cardiac structures. Making the sheets 24, 26 different sizes may assist in providing optimal occlusion of a defect, without affecting other structures of the heart which may be nearby.

The other parts of the stabilization device 10 are likewise formed of suitable materials. More specifically, the center posts 12, 14 may be formed of platinum-iridium or titanium, and the end caps 22 may be formed of titanium. The puller arms 20 may be made of Nitinol, platinum-iridium, or titanium. However, the invention is not limited to these materials and any suitably biocompatible materials will suffice.

Though not immediately evident in FIGS. 1 and 2, the arms 18 vary slightly in length. To allow the device 10 to be retrievable and to ensure that the device 10 fits into as small a diameter catheter as possible, it is important that the arms 18 are not of a length that results in the end caps 22 clustering at the same location when loaded inside the catheter. If the end caps 22 are clustered in the same location when the device 10 is inside the catheter, the device 10 may become too bulky to allow it to be easily moved through the catheter. Thus, varying the arm 18 length allows the device 10 to fit more easily into a small diameter catheter when the device 10 is folded because the end caps 22 do not cluster. In addition, though shown with six arms 18, the device 10 is not so limited. Rather, the device 10 may be comprised of four arms, or may be comprised of anywhere from five, six, eight, ten, or even more arms.

The puller arms 20 are connected to the floating center post 14 by passing the arms 20 through holes drilled into the floating center post 14. The ends of the puller arms 20 are then inserted into end caps 22 through which the hoop 28 has been threaded. Inserting the ends of the puller arms 20 into the end caps 22 connects the puller arms 20 to the hoop 28.

The number of puller arms 20 may be varied. In order to keep the mass of the device 10 minimal, however, the device 10 preferably has a small number of puller arms 20. The device shown in FIGS. 1 and 2 has four puller arms 20. The arms are spread out along the hoop so that they may collapse the hoop 28. The arms should be arranged so that each arm 20 pulls on a different location on the hoop 28 so that the hoop 28 collapses. To ensure that the hoop 28 easily collapses, the puller arms 20 may be offset from one another by 45°. However, the device 10 is not so limited and the puller arms 20 may be offset from one another by anywhere from 5° to 180°.

Because delivery and retrieval occurs through the right chamber of the patient's heart, the device 10 needs only to be graspable on the right side, which is attached to the delivery or retrieval device. For this reason, only one set of puller arms 20 is required. If desired, additional sets of puller arms 20 may be added, but the addition would increase the mass of the device 10.

The puller arms 20 are preferably thinner than the arms of the fixation devices 16, 34 and do not add much mass to the device 10 so the device 10 may fit through a small diameter catheter. The puller arms 20 do not experience constant stress once the device 10 is deployed, as the arms 18 of the fixation devices 16, 34 do. However, the puller arms 20 must be strong enough to withstand stress during delivery and loading. Because the puller arms 20 must be flexible and do not need to exert constant pressure after the device 10 is deployed like the arms 18 of the fixation devices 16, 34 do, the puller arms 18 may be constructed of lighter material. Also, the puller arms 20 must be long enough to be capable of collapsing the hoop 28 but their length should be kept to a minimum so that they lie as close as possible to the septum after the device 10 is deployed and in place. One way to ensure that the puller arms 20 lie close to the septum is to heat shape the puller arms 20 so that they lie flat once the device 10 is deployed and in place.

The puller arms 20 allow the device 10 to be loaded or reloaded for deployment. To load the device 10 into a catheter, the right side (the side that sits in the right side of the patient's heart) of the device must be folded backwards 36, with the hoops 28 facing axially away from the left side. The puller arms 20 transmit a pulling force from the knob 32 on the floating center post 14 to the hoop 28 to pull the right side backwards 34 to pull back the right side so that the right side is ready for loading and subsequent deployment.

Another feature of the occlusion device 10 is that it is fully retrievable. In situations where the occlusion device 10 is not properly deployed and must be retrieved into the catheter, it is possible to withdraw the occlusion device 10 back into the catheter by grasping the knob 32 of the floating center section 14 and pulling. When the pulling arms 20 are pulled by the floating center section 14, the right side of the device 10 collapses and can be withdrawn into a catheter. Subsequently, the device 10 may be deployed or redeployed.

FIG. 3a-3e are diagrammatic views which demonstrate the automatic loading system of the invention. Though FIGS. 3a through 3e show how to load a device, the same procedure applies if the device 10 must be retrieved, reloaded, and/or redeployed in situ.

Figure 3A:
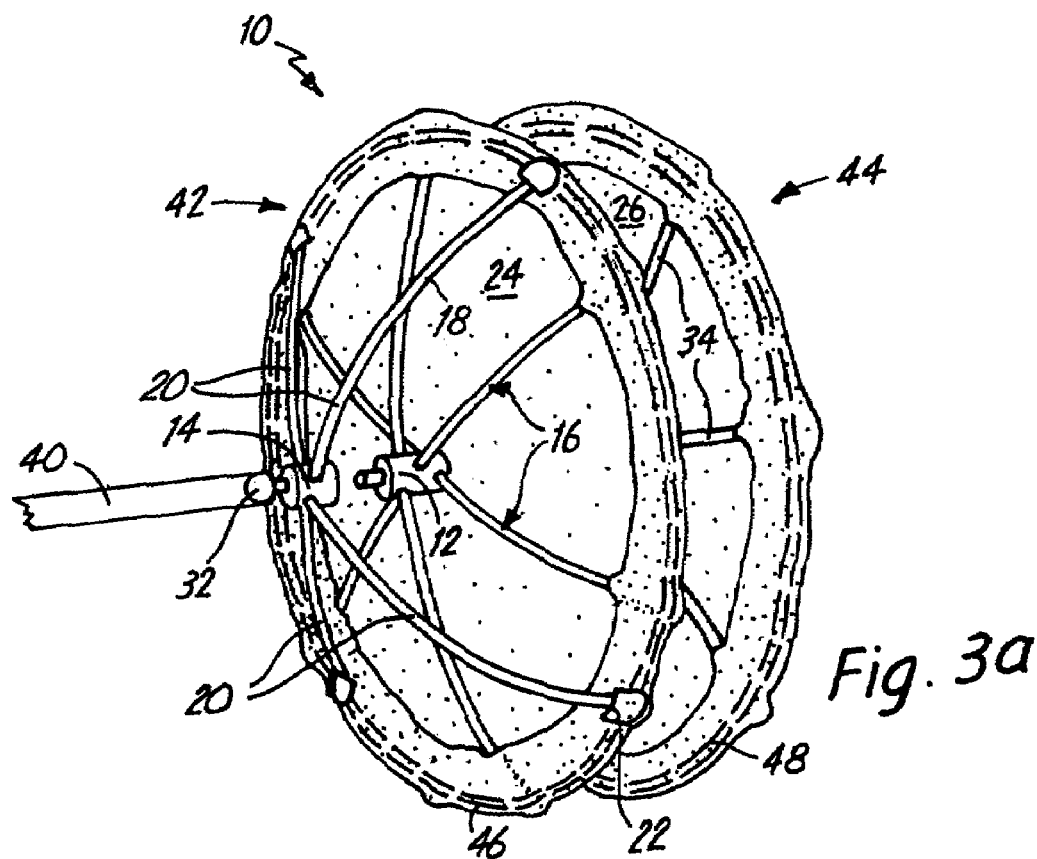
FIGS. 3a-3e are a diagrammatic series showing how the device may be loaded or reloaded.

Shown from left to right in FIG. 3a is a delivery device 40, and the occlusion device 10 comprising the fixed center post 12, the floating center post 14, puller arms 20, the fixation devices 16, 34, sheets 24, 26, and endcaps 22. The occlusion device 10 comprises a right side 42, a left side 44, and a right and left hoop 46, 48. The right side 42 is so named because it is configured for placement in the right side of a patient's heart once the occlusion device 10 is deployed. The left side 42 is so named because it is configured for placement in the left side of a patient's heart once the occlusion device 10 is deployed.

FIG. 3a shows the occlusion device 10 before the occlusion device 10 is loaded into a catheter. Both the left and right sides 42, 44 of the device 10 are shaped to bias the edges of the sheets 24, 26 inward. As a result, each side 42, 44 assumes an umbrella-like shape. When the device 10 is in place in the heart, shaping each side 42, 44 with an inward bias helps ensure the sheets 24, 26 fit snugly against the septum around the defect. This pressure exerted by the two sides 42, 44 creates a seal around the defect. The floating center post 14 sits slightly up and away from the right side 42 of the device and the puller arms 20 are slightly curved. Delivery device 40 includes a grasping mechanism (not shown) for engaging and holding knob 32, so that arial force can be applied to device 10 through delivery device 40.

Figure 3B:
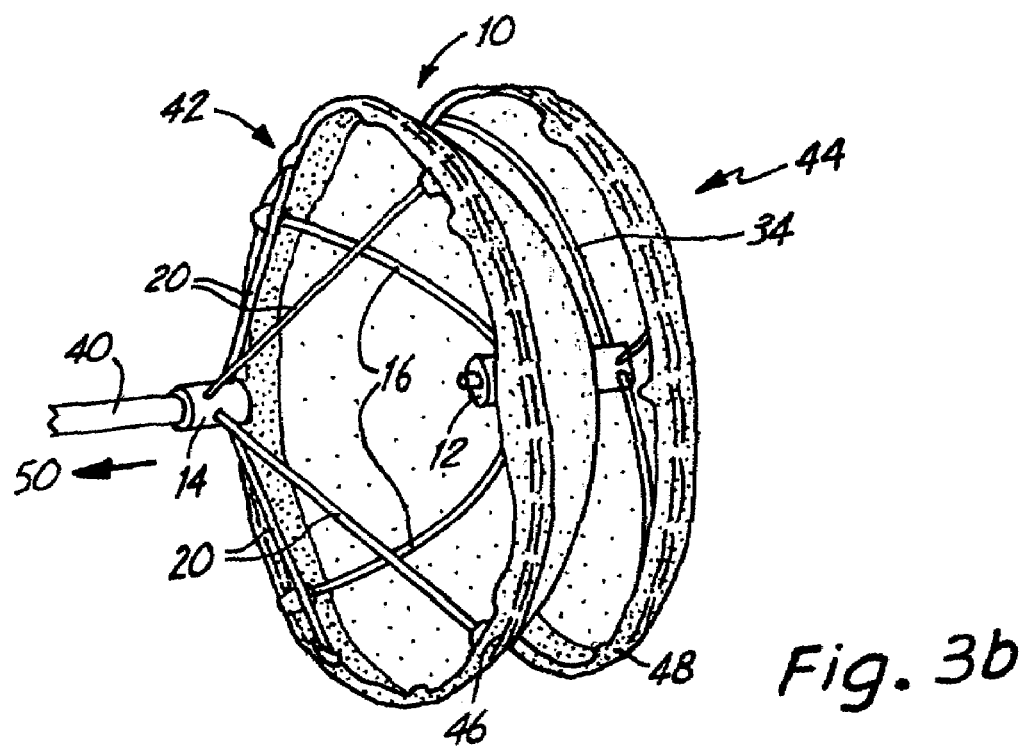

FIG. 3b shows the first step of loading the occlusion device 10 into a catheter. The delivery device 40 is pulled into a catheter in the direction of arrow 50. As shown in FIG. 3b, when the delivery device 40 is pulled, the floating center post 14 engages the puller arms 20 because they are attached to the floating center post 14. The puller arms 20 are attached to the right hoop 46 via end caps 22. Thus, as demonstrated in FIG. 3b, the pulling arms 20 can cause the right hoop 46 to pull away from the left side 44, and cause the right hoop 46 to begin to collapse backwards, towards the direction of the pulling force 50.

To load the device 10, a physician pulls on the delivery device 40 which pulls on the floating center post 14. When the floating center post 14 is pulled by the delivery device 40, the puller arms 20 begin to lose curvature as the floating center post 14 is pulled away from the right side 42 of the device 10. As the puller arms 20 are pulled by the floating center post 14, the puller arms 20 straighten and start to pull on the hoop 46. As mentioned previously, the puller arms 20 are attached to the hoop 46 via end caps 22, so the force on the puller arms 20 transmits to the end caps 22 and thus, to the right hoop 44. Once the puller arms 20 straighten, the arms 20 begin to pull on the hoop 46 and pull the hoop 46 backwards, away from the left side 44. As the hoop 46 is pulled back, the fixation devices 16, 34 flex back also because they are attached to the hoop 46 at the end caps 22.

Figure 3C:
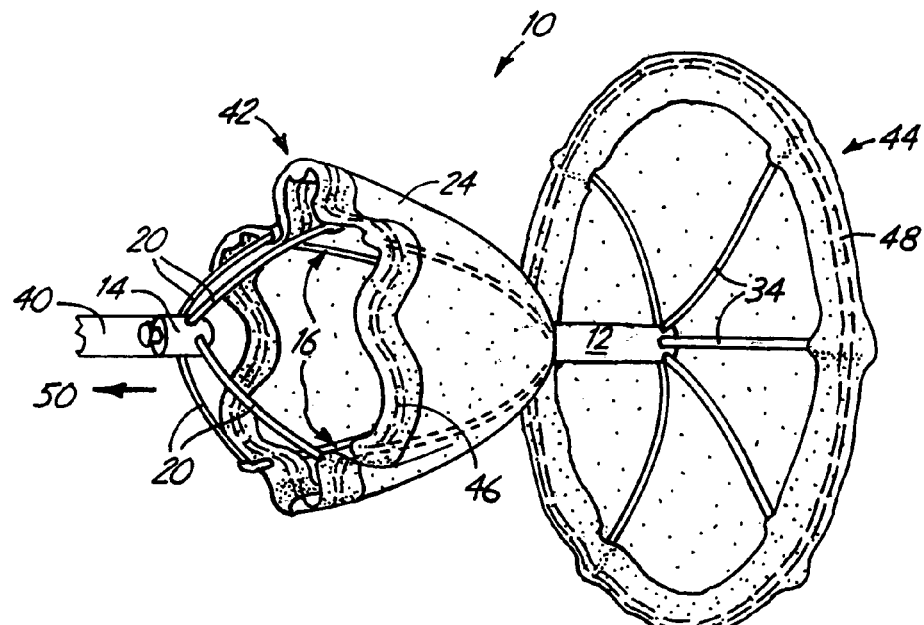

In FIG. 3c, the pulling force continues to be transmitted from the delivery device 40 through the floating center post 14 and puller arms 20 to the right hoop 46. The center post 14 is farther away and therefore the arms 20 pull more on the device right side 42 of the device 10. The force from the puller arms 20 collapses the right hoop 46 further. As the right hoop 46 is pulled, the hoop 46 begins to buckle and collapse and the diameter of the hoop 46 is reduced. Because the arms 18 and hoop 46 are formed of flexible material, as the puller arms 20 move in the direction of the arrow 50, the arms 18 of the fixation devices begin to bend. As a result, the arms 18 no longer bias the sheet 24 forward, but begin pulling on the center post 14 causing the center post 14 to move away from the fixed center post 12. At the same time, the puller arms 20, which are connected to the center post 14 and the right hoop 46, start to fold the right side 42 of the device 10 in the direction of the arrow 50.

Though the right side 42 is collapsing, the left side 44 remains expanded. When the device 10 is loaded by a physician, the physician grasps the left side 44, holding it stationary, the delivery device 40 is pulled to collapse the right side 42. If the device 10 were being removed and reloaded in situ, the left side 44 would be cupping the septum and thus, the left side 44 would not immediately respond to the pulling force because it would be held in place by the septum.

Figure 3D:
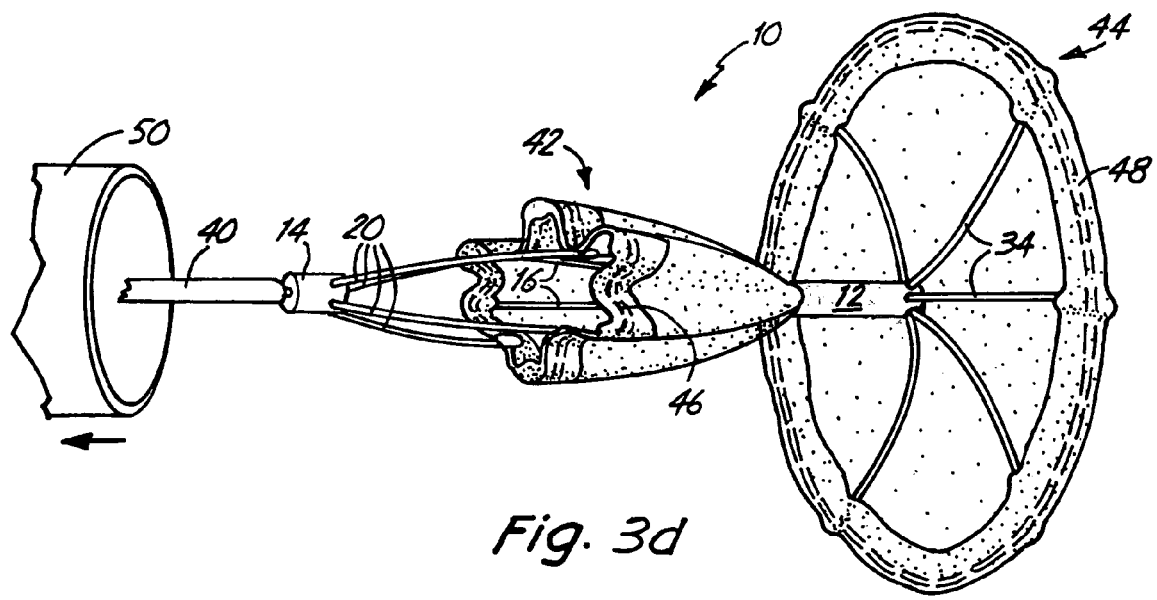

FIG. 3d shows the right side 42 fully collapsed and ready to be pulled into a catheter 50. The continued pulling force has collapsed the right hoop 46 further, increasing the buckling of the right hoop 46. The puller arms 20 are fully extended and are now almost horizontal. Because the arms 16 and sheet 24 are flexible, the arms 16 and sheet 24 collapse as well. In FIG. 3D, the pulling force has collapsed the right hoop 46 to the point that the right side 42 of the device 10 is small enough to be pulled into a catheter 50.

Figure 3E:
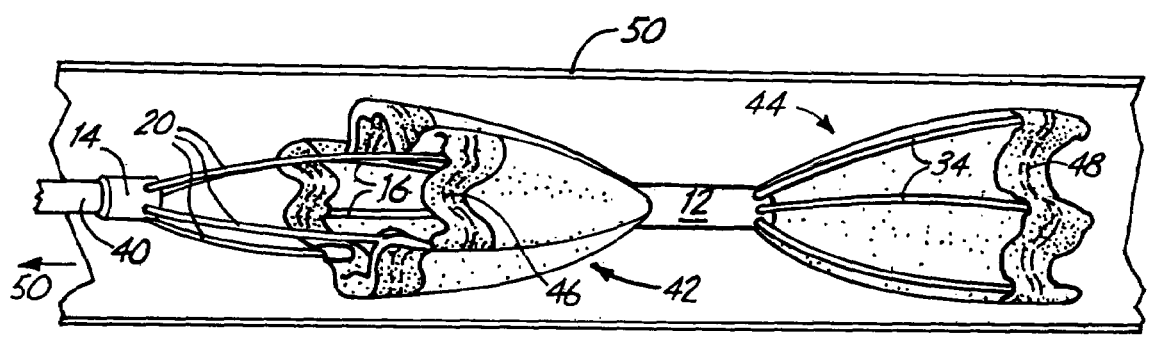

FIG. 3e shows the device 10 loaded into the catheter 50. The right side 42 of the device 10 is pulled into the catheter 50, the left side 44 has trailed and is pulled into the catheter 50 also. The left side 44 collapses backwards as it enters into the catheter 50 because the perimeter of the catheter 50 puts pressure on the fixation devices 34 of the left side 44 as the device 10 is pulled into the catheter 50. In response to the constraints of the catheter 50, the fixation devices 34 of the left side 44 collapse as the left side 44 is pulled into the catheter 50. At this point, the device 10 is ready for deployment.

The design of the present invention allows the device 10 to be loaded or reloaded easily, which has many advantages. The physician does not need to manually collapse the device 10 to ready it for deployment, which makes initial loading easier. If the device 10 has been deployed and must be retrieved and redeployed, the physician can retrieve, reload, and redeploy the device without first having to maneuver the device 10 out of the body to be reloaded. Most devices do not reload when retrieved and thus, must be maneuvered back out of the patient's body to be reloaded for redeployment. When the device 10 is pulled back through the catheter, out of the body, reloaded and redeployed, the integrity of the device 10 may be compromised. Thus, it is preferable to be able to reload and redeploy the device without having to maneuver it through the patient's body again. In addition, the ability to reload and immediately redeploy occlusion device 10 reduces the procedure time. Consequently, the present invention can save time, cost, and additional risk to the patient.

FIG. 4 shows the floating center post 14 and the fixed center post 12 in greater detail. Shown is the floating center post 14, holes 60 in the floating center post 14 through which puller arms pass, the fixed center post 12, holes 62 in the fixed center post 12, through which fixation devices pass, the grasping knob 32, a pin 64, and a lumen 66. The pin 64 on the fixed post 12 fits into the lumen 66 on the floating post 14.

To advance the device 10 through a catheter, a delivery forceps or other delivery device attaches to the grasping knob 32 on the floating center post 14. To move the device 10 through the catheter, the delivery device pushes the device 10 using the floating center post 14 and the fixed center post 12. For this reason, the floating center post 14 is equipped with a lumen 66 that fits over the pin 64 extending from the fixed center post 12. When pushing the device 10 through the catheter, the lumen 66 connects with the pin 64 of the fixed center post 12.

The connection between the floating center post 14 and fixed center post 12 improves the navigability of the device 10. In particular, the connection of the lumen 66 to the pin 64 improves navigability by making it easier to "steer" the device 10 when the physician advances and maneuvers the device 10 through the body to the treatment site. When the pushing ceases or when the device 10 is pulled, the floating center post 14 separates from the fixed center post 12. Thus, when the floating center post 14 is pulled, the two center posts 14, 12 are no longer in direct contact. The floating center post 14, however, remains connected to the device by the puller arms 20, which are threaded through holes in the floating center post 14. The puller arms 20 also attach to the device 10 at the end caps 22 which are located at the hoops 28. Therefore, the device 10 moves as a whole even though the two center posts 12, 14 are not connected.

FIG. 5 shows an enlarged perspective view of an end cap 22 in place on a hoop. Shown is an end cap 22, a portion of a support hoop 70, a portion of a wire arm 72, which may be either a puller arm or a wire support arm, a hole 74, and an end cavity 76. The support hoop 70 passes through holes 74 drilled crosswise through the end cap 22. The arm 72 is inserted into an end cavity 76 located at the base of the end cap 22.

The end caps 22 cap the ends of arms 72 to protect tissue and prevent unraveling of the wire arms 72 if the arms 72 are stranded. The tip of the end cap 22 is rounded to reduce the potential for trauma to the tissue surrounding a defect. The end caps 22 also serve as an attachment site for the support hoop 40, the fixation devices 16, 34, and the puller arms 20. By providing a link between the wire support arms 72 and the support hoop 70, the end caps 22 assist in providing better distribution of pressure once the device 10 is deployed and is exerting pressure on the tissue surrounding a defect. The end caps 22 also serve to connect the puller arms 20 to the support hoop 40, so that the arms 20 may exert pressure to collapse the device 10 when the device 10 must be loaded or reloaded into a catheter.

FIGS. 6a and 6b are top plan views of a portion of the support hoop 70. FIGS. 6a and 6b show two examples of how a support hoop can be closed so that it forms a circle. FIG. 6a shows an end cap 22, a portion of a support hoop 70, a portion of a wire arm 74, ends of the support hoop 80, and an end cavity 76.

The support hoop 70 is typically formed of a single wire. To form the hoop 70, the ends of the wire must be connected in order to form a 360° hoop. The support hoop 70 may be connected after it has been threaded through the end caps 22. In FIG. 6a, the ends of the support hoop 80 meet after passing through holes 74 in the end cap 22 so that the ends of the wire hoop 80 are connected inside the end cap 22. The ends of the support hoop 80 are secured in the end cap 22 by any suitable method, such as crimping, welding, or adhesive. By joining the ends of the support hoop 80 inside an end cap 22, no additional material must be added to the occlusion device 10, thereby keeping the size and weight of the device 10 to a minimum.

FIG. 6b shows a second example of how a support hoop may be closed. FIG. 6b shows a portion of a support hoop 70 which has been closed inside a coupler 82. Shown is a portion of a support hoop 70, ends of the support hoop 80, and a coupler 82. In this example, the coupler 82 is a small hollow tube with a diameter slightly larger than that of the wire used to construct the support hoop 70. The ends of the support hoop 80 are inserted in the coupler 82 where they meet. The coupler 82 can then be crimped or welded so that the ends of the support hoop 80 remain inside the coupler 82.

Other possible methods of joining the ends of the support hoop 80 may include crimping the ends 80 together or welding the ends 80 together without the use of an end cap 22 or coupler 82.

Figure 7:
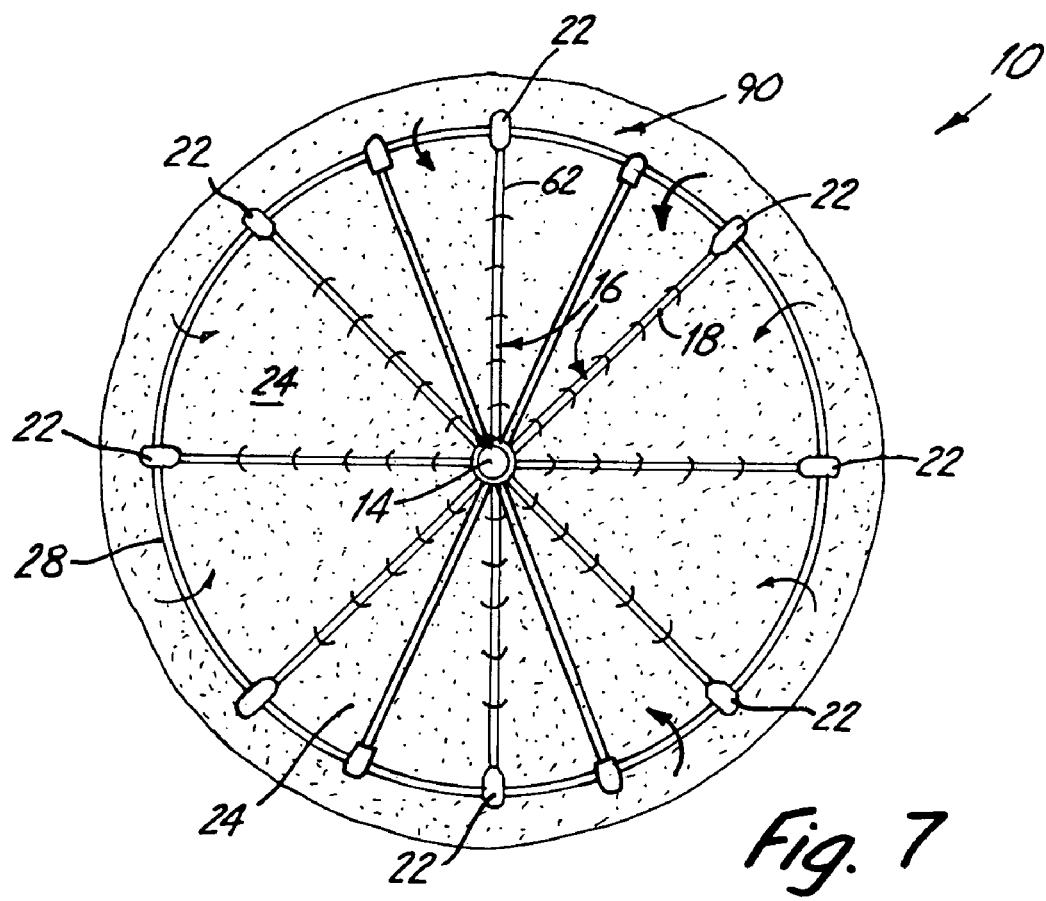
FIG. 7 is a top view of an occlusion device having a hoop which demonstrates how a sail is attached to the support frame and hoop.

FIG. 7 is a top view of an occlusion device 10 demonstrating how the right and left sheets 24, 26 may be attached to the device 10. Shown is the floating center post 14, right wire fixation devices 16 comprising wire arms 18, end caps 22, the right sheet 24, and the support hoop 28. Also shown are sutures 62 and a reinforcement edge material 90.

The sutures 92 may be used to attach the right sheet 24 to the wire arms 18. Though not shown, the second sheet 26 may be attached to the wire arms 18 in the same manner. In this example, the sutures 92 traverse the wire arms 18, attaching the sheet 24 to the arms 16. In addition to suturing, the foam sheets may be connected to the arms 18 using any suitable method, such as bonding, adhesive, heat treating, or laminating.

In FIG. 7, the diameter of the right sheet 24 is slightly larger than that of the support hoop 28. The portion of the right sheet 24 which extends beyond the support hoop 28 constitutes the reinforcement edge material 90. The reinforcement edge material 90 allows this portion of the sheet to be folded over the support hoop 28 to form a reinforced edge of double material around the perimeter of the device 10. Once the reinforcement edge material 90 has been folded over the support hoop 28, it can be held in place such as suturing, bonding, adhesive, heat treating, laminating, or other suitable method.

Alternatively, the reinforced edge 90 is created using a separate sheet of foam formed in a ring. The foam ring is sized to allow it to fold over the perimeter of the device 10 and support hoop 28. The foam ring may be attached to the sheet 24 using any suitable method such as suturing, bonding, adhesive, heat treating, or laminating.

Once attached, the reinforcement edge material 90 covers the exposed edges of the occlusion device 10. The reinforcement edge 90 acts as a cushion between the exposed metal edges of the occlusion device 10 and the tissue surrounding the defect, providing extra protection from pressure that the device 10 exerts on the tissue.

The reinforced edge 90 also secures the sheets 24, 26 to the device 10. Often, in order to adequately seal the defect, the wire arms 18 must bend to accommodate the contours of the heart. Because the sheets 24, 26 are sewn to the wire arms 18, the sheets 24, 26 must accommodate the bending of the wire arms 18. In locations where some of the wire arms 18 are bent by the contours of the heart, a portion of the sheets 24, 26 may be stretched so that it experiences constant tension. This tension may cause the sheets 24, 26 to tear, especially where the sutures 92 are located. If the sheets 24, 26 tear, the sealing ability of the occlusion device 10 may be compromised. The reinforced edge 90 helps to prevent the first and second sheets 24, 26 from tearing at the areas where the sheets 24, 26 are attached to the device 10 or are sutured. Because the reinforcement edge 90 overlaps the hoop 28 and is then affixed to the rest of the sheet 24, 26, it adds an additional 360° of continuous attachment of the sheets 24, 26 to the frame of the device 10 reducing the likelihood of tearing or detachment. The additional foam material along the perimeter of the device helps to distribute the tension on the sheets 24, 26 along a continuum, instead of focusing tension at discrete attachment sites like the suture points.

Figure 8:
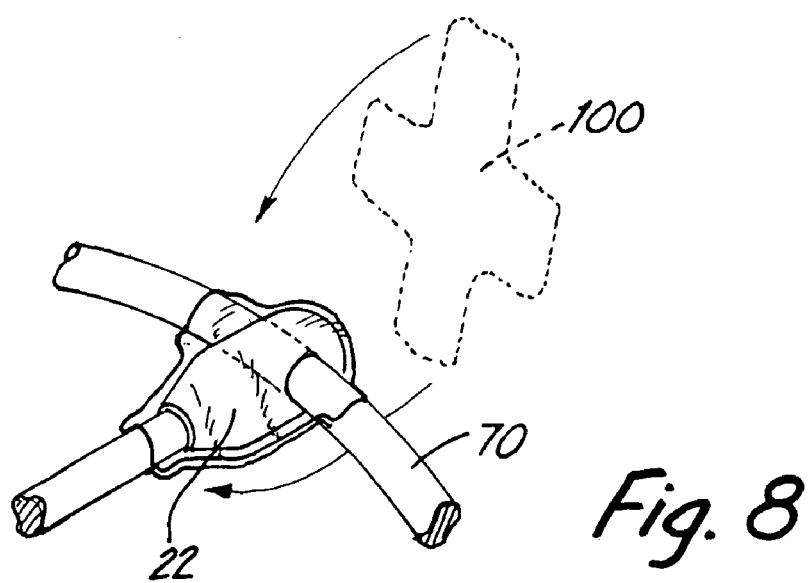
FIG. 8 is a perspective view of a foam patch in place on an end cap in an occlusion device.

FIG. 8 demonstrates an alternative method of reinforcing attachment of the foam sheets to the occlusion device 10. Shown is a patch 100, a portion of a support hoop 70, a portion of a wire arm 72, and an end cap 22. The patch 100 is constructed of foam and is configured to fit over the end cap 22. In this example, the patch 100 is shaped like a cross which enables it to cover both sides of the end cap 22 and a small portion of the support hoop 70 where the hoop 70 extends out of the end cap 22. The patch 100 may be secured by sutures, heat treatment, laminating, or another suitable method.

In addition to reinforcing the sheets, the patch 100 also acts as a cushion between the metal end caps 22 of the occlusion device 10 and the tissue surrounding the defect, providing extra protection from pressure that the device 10 exerts on the tissue. The patch 100 also reduces the amount of metal to tissue contact.

Although the present invention has been described with reference to preferred embodiments, workers skilled in the art will recognize that changes may be made in form and detail without departing from the spirit and scope of the invention.

The invention claimed is:

1. An occlusion device having a right end and having a left end that is insertable through a septal defect, the occlusion device comprising:
   a center post extending to the left end of the occlusion device;
   a right occluding body comprising a first plurality of arms attached to the center post at radially innermost ends, wherein the center post extends through the right occluding body;
   a left occluding body comprising a second plurality of arms attached to the center post at radially innermost ends, the left occluding body being located closer to the left end of the occlusion device and the right occluding body being located closer to the right end of the occlusion device;
   a plurality of puller arms attached to the right occluding body for collapsing the right occluding body from a fully radially open state to a radially collapsed state, the puller arms being located on a right side of the right occluding body;
   a floating center located at the right end of the occlusion device external to the right occluding body and connected to the puller arms at a position to the right of both the right and left occluding bodies; and
   a grasping knob located on a right end of the floating center, wherein the floating center is engaged with the center post without being latched when the right occluding body is in its fully radially open state, and is movable away to the right from the center post by force applied to the grasping knob in a direction to the right to cause the puller arms to radially collapse the right occluding body.

2. The mechanism of claim 1 wherein the puller arms are constructed of nickel titanium.

3. The mechanism of claim 1 wherein an angle between adjacent puller arms is between about 5° and about 180°.

4. The mechanism of claim 1 wherein the floating center comprises an axially extending groove which reversibly connects with an axially extending pin extending from the center post.

5. The mechanism of claim 1 wherein the floating center is constructed of platinum-iridium.

6. The mechanism of claim 1 wherein the center post is constructed of platinum-iridium.

7. A septal occlusion device having a right end and having a left end insertable through a septal defect, the septal occlusion device comprising:
   right and left occluding bodies comprising right and left collapsible support frames, respectively, each support frame comprising a plurality of support arms attached at radially innermost ends to a center section which extends though the right occluding body to a left end of the occlusion device, the right occluding body positioned to the right of the left occluding body, the left occluding body being insertable in a radially collapsed state through a septal defect so that when the septal occlusion device is deployed within a heart of a patient to close a septal defect in the heart, the right occluding body is located in a right chamber of the heart and the left occluding body is located in a left chamber of the heart;
   a plurality of puller arms attached to the right occluding body;
   a floating center positioned to the right of both the right and left occluding bodies, the center section and the plurality of puller arms, the floating center being external to the right occluding body; and
   a grasping knob located at the right end of the floating center, which, when pulled away to the right from the center section, pulls the puller arms to collapse the right collapsible support frame from a fully radially open state where the floating center engages the center section without being permanently connected to the center section to a radially collapsed state such that the device is capable of being retrieved.

8. The device of claim 7 wherein the arms are constructed of nickel titanium.

9. The mechanism of claim 7 wherein an angle between adjacent puller arms is between about 5° and about 180°.

10. The device of claim 7 wherein the floating center comprises an axially extending groove which reversibly connects with an axially extending pin extending from the center section.

11. The device of claim 7 wherein the floating center is constructed of platinum-iridium.

12. The device of claim 7 wherein the center section is constructed of platinum-iridium.

13. The device of claim 7 wherein the support frames each comprise a wire hoop attached to radially outermost ends of the plurality of support arms.

14. The device of claim 13 wherein the support arms are constructed of stranded wire.

15. An occlusion device having a right end and a left end, the left end being insertable through a septal defect, the occlusion device comprising:
   a center section extending in an axial direction to the left end of the occlusion device;
   right and left elastic shape memory fixation devices each comprising a plurality of arms attached to the center section at radially innermost ends such that each fixation device extends radially outward from the center section;
   right and left sheets attached to the right and left fixation devices, respectively so that the left sheet is closer to the left end of the closure device, and the right sheet is closer to the right end of the closure device, wherein the center section extends through the right sheet;
   a plurality of puller arms connected to the right fixation device, the puller arms being positioned on a right side of the right fixation device;
   a floating center positioned to the right of the center section and to the right of both the left and right sheets, and connected to the puller arms, the floating center being external to the right fixation device; and
   a grasping knob located at the right end of the floating center, which, when pulled away from the center section, pulls the puller arms to collapse the right fixation device, and right sheet from a fully radially open state where the floating center engages the center section without being permanently connected to the center section to a radially collapsed state such that the device is capable of being retrieved.

16. The occlusion device of claim 15 wherein the arms are constructed of nickel titanium.

17. The mechanism of claim 15 wherein an angle between adjacent puller arms is between about 5° and about 180°.

18. The occlusion device of claim 15 wherein the floating center comprises an axially extending groove which reversibly connects with an axially extending pin extending from the center section.

19. The occlusion device of claim 15 wherein the floating center is constructed of platinum-iridium.

20. The occlusion device of claim 15 wherein the center section is constructed of platinum-iridium.

21. An occlusion device for occluding a septal defect, the occlusion device having a right end and having a left end insertable through the septal defect, the occlusion device comprising:
- a center post extending to the left end of the occlusion device;
- a right occluding body comprising a first plurality of arms attached to the center post at radially innermost ends such that the right occluding body extends radially outward from the center post, and a first sheet attached to the first plurality of arms, wherein the center post extends through the first sheet;
- a left occluding body comprising a second plurality of arms attached to the center post at radially innermost ends such that the left occluding body extends radially outward from the center post, and a second sheet attached to the second plurality of arms;
- a plurality of puller arms connected to the right occluding body and positioned to the right of the right occluding body;
- a floating center positioned to the right of both the right and left occluding bodies, the center post, and to the right of the plurality of puller arms, the floating center being external to the right occluding body; and
- a grasping knob located at the right end of the floating center so that, when the grasping knob and floating center are pulled away from the center post, the floating center pulls the puller arms to collapse the right occluding body from a fully radially open state where the floating center engages the center post without being permanently connected to the center post to a radially collapsed state such that the device is capable of being retrieved.

22. The occlusion device of claim 21 wherein the arms are constructed of nickel titanium.

23. The mechanism of claim 21 wherein an angle between adjacent puller arms is between about 5° and about 180°.

24. The occlusion device of claim 21 wherein the floating center comprises an axially extending groove which reversibly connects with an axially extending pin extending from the center post.

25. The occlusion device of claim 21 wherein the floating center is constructed of platinum-iridium.

26. The occlusion device of claim 21 wherein the center post is constructed of platinum-iridium.

27. An occlusion device for the closure of a physical anomaly, the occlusion device having a right end and having a left end that is insertable through the physical anomaly, the occlusion device comprising:
- a center post extending to the left end of the occlusion device;
- a right set of support arms attached at radially innermost ends to the center post such that the right set of support arms extends radially outward from the center post;
- a right sheet attached to the first set of support arms, wherein the center post extends through the right sheet;
- a left set of support arms attached at radially innermost ends to the center post such that the left set of support arms extends radially outward from the center post;
- a left sheet attached to the second set of support arms;
- a floating center located at the right end of the device, to the right of the center post, the right and left sets of support arms and the right and left sheets, the floating center being external to the right sheet;
- a grasping knob located on a right end of the floating center; and
- a plurality of puller arms attached to the floating center and first set of support arms which radially collapse the right set of support arms and the right sheet from a fully radially open and deployed state where the floating center is engaged with the center post without being permanently connected to the center post to a radially collapsed state when the grasping knob is pulled away in a right direction from the center post.

28. The occlusion device of claim 27 wherein the arms are constructed of nickel titanium.

29. The mechanism of claim 27 wherein an angle between adjacent puller arms is between about 5° and about 180°.

30. The occlusion device of claim 27 wherein the floating center comprises an axially extending groove which reversibly connects with an axially extending pin extending from the center post.

31. The occlusion device of claim 27 wherein the floating center is constructed of platinum-iridium.

32. The occlusion device of claim 27 wherein the center post is constructed of platinum-iridium.

33. An occlusion device having a right end and having a left end that is insertable through a septal defect, the occlusion device comprising:
- a right collapsible support frame comprising a plurality of arms;
- a left collapsible support frame comprising a plurality of arms;
- a center post attached to radially innermost ends of the right and left support frames and extending to the left end of the occlusion device;
- a right sheet attached to the right collapsible support frame, the center post extending through the right sheet;
- a left sheet attached to the left collapsible support frame, the left sheet being closer to the left end of the occlusion device and the right sheet being closer to the right end of the occlusion device;
- a plurality of puller arms attached to the right support frame and located to the right of the right support frame;
- a floating center located at the right end of the occlusion device, and located to the right of the center post, the right and left support frames and the right and left sheets, the floating center being external to the right support frame; and
- a grasping knob located on a right end of the floating center, which, when pulled to the right away from the center post, causes the puller arms to collapse the right collapsible support frame from a fully radially open state where the floating center engages the center post without being permanently connected to the center post to a radially collapsed state such that the device is capable of being retrieved.

34. The occlusion device of claim 33 wherein the arms are constructed of nickel titanium.

35. The mechanism of claim 33 wherein an angle between adjacent puller arms is between about 5° and about 180°.

36. The occlusion device of claim 33 wherein the floating center comprises an axially extending groove which reversibly connects with an axially extending pin extending from the center post.

37. The occlusion device of claim 33 wherein the floating center is constructed of platinum-iridium.

38. The occlusion device of claim 33 wherein the center post is constructed of platinum-iridium.

* * * * *

UNITED STATES PATENT AND TRADEMARK OFFICE
CERTIFICATE OF CORRECTION

PATENT NO.      : 7,658,748 B2                           Page 1 of 1
APPLICATION NO. : 10/668445
DATED           : February 9, 2010
INVENTOR(S)     : Joseph A. Marino et al.

It is certified that error appears in the above-identified patent and that said Letters Patent is hereby corrected as shown below:

Col. 11, Line 51
 Delete "though"
 Insert --through--

Signed and Sealed this
Fourteenth Day of June, 2011

David J. Kappos
*Director of the United States Patent and Trademark Office*